United States Patent [19]
Pontecorvo et al.

[11] Patent Number: 4,906,638
[45] Date of Patent: Mar. 6, 1990

[54] DEXTROMETHORPHAN POTENTIATOR FOR ANTICONVULSANT COMPOSITION AND METHOD

[75] Inventors: Michael J. Pontecorvo, Belcamp; John W. Ferkany, Baltimore, both of Md.

[73] Assignee: Nova Pharmaceutical Corporation, Baltimore, Md.

[21] Appl. No.: 136,751

[22] Filed: Dec. 22, 1987

[51] Int. Cl.$^4$ ............................................. A61K 31/44
[52] U.S. Cl. .................................................. 514/282
[58] Field of Search ........................................ 514/282

[56] References Cited

U.S. PATENT DOCUMENTS 4,694,010  9/1987  Musacchio et al. ................ 514/304

OTHER PUBLICATIONS

Frank C. Tortella and Jose M. Musacchio, Dextromethorphan and Carbetapentane: Centrally Acting Non–Opioid Antitussive Agents With Novel Anticonvulsant Properties, *Brain Research*, 383(1986)314–318.

John Church, David Lodge and Stephen C. Berry, Differential Effects of Dextrorphan and Levorphanol on the Excitation of Rat Spinal Neurons by Amino Acids, *Eur. J. Pharmacol.*, 111(1985)185–190.

Laurane G. Mendelsohn, Gail A. Kerchner, Vin Kalra, Dennis M. Zimmerman and J. David Leander, Phencyclidine Receptors in Rat Brain Cortex, *Biochem. Pharmacol.*, vol. 33, No. 22, pp. 3529–3535, (1984).

*Primary Examiner*—Stanley J. Friedman
*Attorney, Agent, or Firm*—Breneman & Georges

[57] ABSTRACT

A pharmaceutical composition comprises an anti-epileptic drug that does not inhibit, enhance or otherwise modify dextromethorphan binding to the central nervous system dextromethorphan receptor and an effective amount of dextromethorphan to potentiate the anticonvulsant activity of the drug. Other related compounds similar to dextromethorphan which inhibit or enhance dextromethorphan binding to the dextromethorphan site in the brain are also suitable as potentiating agents for the anticonvulsants. A method of treating epilepsy and other convulsions include the steps of introducing to the patient an effective amount of the compound comprising an anti-epileptic drug and potentiating amount of dextromethorphan or one of the related compounds.

10 Claims, No Drawings

DEXTROMETHORPHAN POTENTIATOR FOR ANTICONVULSANT COMPOSITION AND METHOD

CROSS REFERENCE TO RELATED APPLICATION

The present application is related to a co-pending application entitled DEXTRORPHAN POTENTIATOR FOR ANTICONVULSANT COMPOSITIONS AND METHOD, Ser. No. 136,564 filed concurrently herewith.

BACKGROUND OF THE INVENTION

1. Field Of The Invention

The present invention relates to a novel combination comprising dextromethorphan in combination with a suitable anti-epileptic drug. More specifically the invention is directed to a pharmaceutical combination and method of treating epilepsy and other convulsions by introducing to the patient an effective amount of a composition comprised of dextromethorphan or one of the similarly related compounds as a potentiating agent in combination with at least one known anti-epileptic drug which does not either inhibit or enhance binding at the [$^3$H]dextromethorphan receptor site in the central nervous system, but does act either to inhibit excitatory amino acid neutrotransmission or to otherwise reduce neutronal excitability.

2. Description Of The Prior Art

In recent years the field of medicine has had varying success in treating epileptic seizures. Most types of seizures, including induced generalized or focal seizures, can be treated with one of several anti-epileptic hydantoins and in particular diphenylhydantoin (DPH) commonly referred to as phenytoin or dilantin. Dilantin is the registered trademark of the Parke-Davis Company.

Dilantin has the advantage of usually inhibiting epileptic activity without causing a general depression of the central nervous system. Moreover, dilantin can limit the development of maximal seizure activity and reduce the spread of the seizure process from an active focus. Because of these desirable characteristics dilantin has been successfully used for many years as an anticonvulsant in the treatment of epilepsy.

The use of dilantin, as well as many other anticonvulsant agents, has been somewhat limited, however, since most effective anticonvulsants possess the distinct disadvantage of being toxic at some concentrations. Although the effectiveness of dilantin in treating seizures increases with dosage, the adverse toxic effects also increase to an unacceptable and often times dangerous level. Many of these adverse toxic effects further increase with the length of exposure and vary with the mode of administration of the anticonvulsant thereby further limiting their use and necessitating the careful monitoring of the patient and constantly altering the medication and procedures.

The dose-dependent toxic effects associated with the continued use of dilantin, as well as other anticonvulsant hydantoins, include cerebellar vestibular effects (nystagmus, ataxia and diplopia vertigo) and central nervous system disturbances such as blurred vision, mydriasis and hyperactive tendon reflexes. Behavioral changed that have been associated with the use of dilantin include hyperactivity, confusion, dullness, drowsiness and hallucination. Further adverse toxic effects include increased frequency of seizures, peripheral neuropathy, gastrointestinal distress, gingival hyperplasia, osteomalacia, megaloblastic anemia, hirsutism, endocrine effects and lymphadenopathy. At very high doses, especially when administered intravenously, dilantin can cause cardiovascular collapse and depression of the central nervous system.

Accordingly, efforts have been made to develop an anti-epileptic drug or anticonvulsant agent having as few side effects as possible while maintaining efficacy. One such effort has been reported in *Brain Res.*, 383:314-318, 1986 by Tortella.

Tortella, aided by earlier work, discovered that their antitussant, dextromethorphan, could serve as an effective anticonvulsant possessing an activity similar to that of dilantin. Dextromethorphan is a potent antitussive agent which has been used for many years in the medical field with few side effects. Most often, dextromethorphan is one of the active ingredients in over-the-counter cough and cold medications. Dextromethorphan is the non-narcotic stereoisomer (enantiomer) of the opioid L-3-methoxy-17-methylmorphinan.

Dextromethorphan when introduced by itself to laboratory test animals at a dose of 30 mg/kg has been shown to provide protection against transauricular maximal electroshock seizure (MES). Dextromethorphan has further been shown to have a somewhat longer protection time against MES than that exhibited by dilantin under standard testing conditions. In addition, Tortella demonstrated that the anticonvulsant potency of dilantin was enhanced ($ED_{50}$ decreased) by co-administration of dextromethorphan in vivo. The use of dextromethorphan as a potentiating agent by Tortella was further extended to include, as potentiating compounds, compounds related to dextromethorphan or other antitussants which inhibit binding of [$^3$H]dextromethorphan to the central nervous system site with high affinity ($IC_{50} < 75$ nM).

The discovery by Tortella was based, at least in part, by earlier findings reported by Craviso and Musacchio in *Mol. Pharmacol.* 23:619-628 and 23:629-640 (1983). These experiments were in part carried out to determine whether antitussants such as dextromethorhan bind at a subset of opiate receptors. Craviso and Musacchio demonstrated high affinity binding of [$^3$H]dextromethorphan to homogenates of guinea pig, rat and mouse lower brainstem ($Kd < 20$ nM). Of significant importance is that the opiate antagonists and agonists did not compete effectively at the same site as dextromethorphan. However, it was shown that some antitussants including carbetapentane, caramiphen and dimethoxanate inhibited binding with $IC_{50}$'s in the 1 to 75 nM range.

Craviso and Mussacchio's report further revealed that the binding of [$^3$H]dextromethorphan was effectively inhibited in vitro by a member of other compounds such as selective antidepressants, phenothiazines, neuroleptics, antihistamines and muscarinic agents and calcium channel blockers ($IC_{50} < 100$ nM). However, the primary importance of their work was in the discovery that the in vitro binding of [$^3$H]dextromethorphan to the central nervous system sites was markedly increased in the presence of certain compounds including noscapine and the anticonvulsant, dilantin. It was noted, however, that the anti-convulsant carbamazepine did not inhibit or enhance [$^3$H]dextromethorphan binding. Additionally, the research fell short, since they were unable to predict which compounds would modify (inhibit or enhance) [³H]dextromethorphan binding at concentrations considered reasonably by those skilled in the art, and which would not. The discovery of Tortella and Musacchio of the anticonvulsant potentiating characteristics of dextromethorphan was, thus, based on the binding site of [³H]dextromethorphan and the binding of compounds, including anticonvulsants, at that site. The discovery of Tortella and Musacchio was, however, rather narrow since the number of suitable potentiating compounds was, thus, limited by the requirements that the potentiators are compounds that inhibit or enhance dextromethorphan binding or otherwise bind to the dextromethorphan site at nM concentrations.

It has been known that dextromethorphan is rapidly metabolized (demethylated) in vivo to yield dextrorohan (DEX) and two lesser metabolites, (+) D-(3)methoxy-morphinan and (+) D-hydroxymorphinan respectively. In rats, dogs and humans the ratio of dextrorphan to dextromethorphan in plasma and urine typically exceeds 100 to 1. The absolute plasma levels of dextromethorphan following 20 to 60 mg p.o. in humans rarely exceeds five nanograms per milliliters whereas the dextrorphan levels are 380 nanograms per milliliter. In man, dextrorphan represents the major metabolite, since the other demethylation products in urine, after eight hours, account for less than 15% of the dose administered. More importantly, the major metabolite, dextrorphan, has a relatively low affinity (2500 nM) for the [³H]dextromethorphan receptor but a relatively high affinity for the [³H]TCP-labeled-NMDA-linked receptor (<10 nM).

Since dextromethorphan is rapidly converted to dextrorphan in vivo, these data raise the possibility that dextromethorphan's anticonvulsant effects may not be directly related to the [³H]dextromethorphan binding site as suggested by Tortella and Musacchio, but may result from the action of metabolites at other (e.g., PCP/NMDA, calcium channels) receptors.

The discovery by Tortella and Musacchio was also severely restricted to the belief that dextromethorphan and the related non-opiate compounds were able to potentiate only anti-epileptic anticonvulsants that enhanced [³H]dextromethorphan binding in the central nervous system. Many commonly used anticonvulsants do not complete, enhance or otherwise interact with dextromethorphan at the [³H]dextromethorphan-labeled binding site at nM concentrations. Of particular importance of the excluded anticonvulsants are compounds such as carbamazepine and excitatory amino acid antagonists and including ketamine, dexoxadrol and pencyclidine. Contrary to the teachings of the prior art, the present discovery indicates that dextromethorphan is effective at potentiating anticonvulsant activity of compounds that do not inhibit or enhance dextromethorphan binding to brain. In addition, the present invention relates to a composition of matter and a method of treating epilepsy using dextromethorphan or its related compounds as a potentiating agent for anticonvulsants such as carbamazepine.

SUMMARY OF THE INVENTION

The disadvantages and limitations of the prior art compositions and methods of treatment for epilepsy and other convulsions are obviated while providing effective anticonvulsant treatment and reducing the adverse side effects of the prior art anticonvulsants.

The present invention is directed primarily to a composition of matter including dextromethorphan and the related compounds as a potentiator for anticonvulsants which do not inhibit, enhance or otherwise modify the binding of dextromethorphan to its receptor. The invention further relates to a method of treating epilepsy using the composition including dextromethorphan and a known anticonvulsant including but not limited to carbamazepine.

Accordingly the present invention relates to a pharmaceutical composition and a method of treatment using that composition which is effective for inhibiting convulsions and treating epilepsy wherein the combination includes dextromethorphan as the potentiating agent.

DESCRIPTION OF THE PREFERRED EMBODIMENT

The present invention is directed to the discovery that dextromethorphan is an effective potentiating agent for anticonvulsants that do not inhibit, enhance or otherwise modify the binding of dextromethorphan to its receptor at concentrations considered reasonable by those skilled in the art ($IC_{50} < 500$ nM).

Dextromethorphan represents a class of non-opiate antitussants which have recently been shown to possess anticonvulsant activity against electrical seizure in laboratory rats. Dextromethorphan has a high affinity (<20 nM) for the [³H]dextromethorphan receptor as do several other non-narcotic, nonaddictive, compounds. Examples of related compounds which bind to the same central nervous system site as dextromethorphan include benztropine, chlorpromazine, perphenazine, flupenthinol fluphenazine, trifluorperazine, dimethoxanate, opipramol, promethazine, pipazethate, carbetapentane, caramiphen trimeprazine, prochlorperazine, cinnarizine roscapine and phenylamine as well as pharmaceutically acceptable derivatives, homologs, isomers, analogs and organic and inorganic salts thereof.

Many of commonly employed anticonvulsants including phenobarbital, diazepam ketamine, dexoxadrol excitatory amino acidantagonists, phencyclidine and carbamazepine do not inhibit or enhance binding of [³H]dextromethorphan to the central nervous system receptor site. In the preferred embodiment of the invention the composition includes the common anticonvulsant carbamazepine (5-H-dibenzepin-(5)-carboxamide).

EXAMPLE I:

Dextromethorphan Potentiation of Carbamazepine Anticonvulsant Effects in the Mouse MES Model To determine the potentiating effect of dextromethorphan on anticonvulsants which do not inhibit or enhance ([³H]dextromethorphan binding at the central nervous system site and in particular carbamazepine, a series of experiments were carried out under controlled conditions. All of the tests were conducted using a standard maximal electroshock (MES) procedure for mice. A transauricular square wave shock of 50 mA, 0.6 msec/pulse, 100 pulses per second was applied for 0.2 seconds. The pilot studies indicated that these parameters produced reliable tonic-clonic seizures in 100 percent of the mice treated with an appropriate vehicle for dextromethorphan or carbamazepine. Ethosuximide was determined to be ineffective in protecting against these seizures since only one in five mice was protected at one half hour and none was protected one hour after i.p. injections of 500 mg/kg. At this dose all mice injected showed signs of sedation, ataxia and gross toxicity.

To determine the potentiating effects of dextromethorphan on the anticonvulsants which do not inhibit or enhance [$^3$H]dextromethorphan binding to its receptor, initial experiments were carried out to determine the effect of dextromethorphan alone. Based on the preliminary determination of time of peak effect dextromethorphan was dissolved in saline and injected in a volume of 0.01 ml/g one-half hour before MES. As revealed in Table 1 dextromethorphan demonstrates a dose dependent anticonvulsant activity.

TABLE 1

DETERMINATION OF THE ANTICONVULSANT EFFECTS OF DEXTROMETHORPHAN (DM) FOLLOWING I.P. ADMINISTRATION TO MICE

| Dose DM (mg/kg) | % Protected |
| --- | --- |
| 5 | 0 |
| 10 | 0 |
| 20 | 8 |
| 25 | 25 |
| 30 | 37.5 |
| 35 | 75 |
| 45 | 87.5 |
| 55 | 100 |

$ED_{50} = 29.21$ (24.1 – 35.4 mg/kg).

The potentiation of carbamazepine anticonvulsant effects by dextromethorphan was examined by methods similar to those used to study dextromethorphan alone. Dextromethorphan was dissolved in saline and carbamazepine was dissolved in 30% polyethylene glycol in distilled water. For combination studies two separate injections were administered. Dextromethorphan was administered one-half hour prior to the MES testing while carbamazepine was administered 15 minutes prior to testing. The absence of tonic hindlimb extension was taken as evidence for seizure protection.

Table 2 shows that dextromethorphan potentiated the anticonvulsant effects of carbamazepine. Thus, the amount of protection (% of animals without seizures) at any given dose of carbamazepine was increased by the co-administration of dextromethorphan. For example, with 20 mg/kg dextromethorphan the % protection increased from 0 to 44% at 3 mg/kg carbamazepine, from 12.5 to 75% at 5 mg/kg carbamazepine and from 44 to 100% at 7 mg/kg carbamazepine. Overall the median effective dose ($ED_{50}$) of carbamazepine was decreased significantly from 7.2 to 2.4 when carbamazepine was combined with 20 mg/kg dextromethorphan.

TABLE 2

DEXTROMETHORPHAN POTENTIATION OF THE ANTICONVULSANT EFFECTS OF CARBAMAZEPINE

| Dose (mg/kg) | % Mice Protected | | |
| --- | --- | --- | --- |
| | CBM | + 10 DM (mg/kg) | + 20 DM (mg/kg) |
| 0 | 0 | 0 | 8 |
| 1 | 0 | — | 25 |
| 3 | 0 | 12.5 | 44 |
| 5 | 12.5 | 50 | 75 |
| 6 | 25 | 62.5 | 75 |
| 7 | 44 | 87.5 | 100 |
| 8 | 50 | | |
| 9 | 75 | 100 | |
| 12 | 100 | | |
| $ED_{50}$ (mg/kg) | 7.2 | 4.8* | 2.4* |
| | (6.3–8.3) | (3.8–6.1) | (1.5–3.7) |

*Different from CBM p <0.05.

TABLE 3

MINIMAL INCREMENT IN CARBAMAZEPINE-INDUCED (CBM) CNS SIDE EFFECTS (ROTOROD-ATAXIA) BY CO-ADMINISTRATION OF DEXTROMETHORPHAN (DM)

| CBM Dose (mg/kg) | % Mice Ataxic | |
| --- | --- | --- |
| | CBM | CBM + 20 DM |
| 0 | 0 | 12.5 |
| 25 | 0 | 12.5 |
| 30 | 18.8 | 25 |
| 35 | 12.5 | 37.5 |
| 40 | 44 | 66.7 |
| 45 | 56 | 75 |
| 50 | 75 | 75 |
| 55 | 62.5 | — |
| 60 | 87.5 | 100 |
| 70 | 87.5 | — |
| $TD_{50}$ | 44.8 | 36.6* |
| | (41.0–48.9) | (33.0–40.6) |

*Significantly different from CBM.

Mice were placed on a rotating bar 30 min following administration of dextromethorphan and/or 15 min following CBM. All mice had previously demonstrated ability to maintain equilibrium for one minute. Mice that were unable to maintain equilibrium for one continuous minute, given 3 opportunities were scored as ataxic.

Note that the doses of dextromethorphan used in these studies (10 and 20 mg/kg) produced little or no protection when administered alone (with 0 CBM). Note also that the maximal therapeutic dose of dextromethorphan produced little increment in carbamazepine's CNS side effects as assessed in a rotorod toxicity test (Table 3). Thus, combination of dextromethorphan with carbamazepine not only augmented the therapeutic potency of carbamazepine, but more than doubled the safety ratio (median toxic/median effective dose = $TD_{50}/ED_{50}$) from 6.2 to 15.2.

EXAMPLE II:

Dextromethorphan Potentiation of 3-(2-carboxypiperazin-4-yl)propyl-1-phosphono Acid (CPP)

Dextromethorphan has also been shown to potentiate anticonvulsants other than carbamazepine and which are thought to interact with receptor sites different from that for dextromethorphan. For example, 3-(2-carboxypiperazin-4-yl)propyl-1-phosphono acid (CPP), is a potent, selective and competitive antagonist of the excitatory amino acid analog N-methyl-D-asparate. When mice (male CF-1; 25–30 g) are administered NMDA (250 mg/kg; IP) animals typically respond with seizure activity consisting of an initial staring, followed in rapid order by hindlimb scratching, increased locomotor activity, rearing behavior, clonic seizures, tonic extension and death. In animals developing seizures, the entire episode evolves in approximately 7–11 minutes.

Referring to Table 4, both CPP and dextromethorphan, administered i.p., afforded protection against N-methyl-D-asparate-induced seizures in mice. Furthermore, the combined administration of dextromethorphan and CPP protected a greater percentage of the animals from seizures than that expected from an additive action of the individually administered doses of CPP and dextromethorphan.

TABLE 4
EFFECT OF DEXTROMETHORPHAN (DM) AND CPP ADMINISTRATION ON N—METHYL-D-ASPARTATE (NMDA) INDUCED CONVULSIONS IN MICE

| CPP (mg/kg) | % Protected | DM (mg/kg) | % Protected | CPP + DM (mg/kg) | % Protected |
|---|---|---|---|---|---|
| 1.5 | 12.5 | 2.5 | 12.5 | 1.5 + 2.5 | 50 |
| 1.5 | 12.5 | 10 | 33 | 1.5 + 10 | 62.5 |
| 2.0 | 37.5 | 2.5 | 12.5 | 2.0 + 2.5 | 62.5 |

Mice (male CF-1, 25-30 g) were administered either CPP or dextromethorphan, alone or in combination, at the indicated dose(s) thirty minutes prior to the administration of NMDA (250 mg/kg). All drugs were dissolved in saline (0.9%; w/v) and delivered by intraperitoneal injection in a volume of 1.0% (w/v) of body weight. Animals were observed for thirty minutes following administration of the convulsant and scored for the presence or absence of tonic/clonic seizures.

Similarly, an interaction of dextromethorphan and CPP was apparent when the agents were examined for an action to prevent MES-induced (50 Hertz; 50 mA; 0.2 sec) seizures in mice (male CF-1; 25-30 g) (Table 5). However, in this instance, a potentiating effect of dextromethorphan on CPP was readily apparent only when low doses of dextromethorphan were administered in combination with anticonvulsant doses of CPP. Administration of higher doses of dextromethorphan were either ineffective to increase the anticonvulsant activity of CPP or, partially attenuated the activity of the excitatory amino acid antagonist as an anticonvulsant.

TABLE 5
EFFECT OF CPP AND DEXTROMETHORPHAN (DM) ON MAXIMAL ELECTROSHOCK INDUCED SEIZURES

| CPP (mg/kg) | % Protected | DM (mg/kg) | % Protected | CPP + DM (mg/kg) | % Protected |
|---|---|---|---|---|---|
| 5 | 25 | 6.6 | 0 | 5 + 6.6 | 66.7 |
| 5 | 25 | 10 | 16.6 | 5 + 10 | 50 |
| 5 | 25 | 27 | 50 | 5 + 27 | 50 |
| 10 | 60 | 6.6 | 0 | 10 + 6.6 | 83 |
| 10 | 60 | 10 | 16.6 | 10 + 10 | 83 |
| 10 | 60 | 27 | 50 | 10 + 27 | 50 |
| 10 | 60 | 30 | 66.6 | 10 + 30 | 83 |

Mice (male CF-1; 25-30 g) were administered either CPP or dextromethorphan alone or in combination at the indicated dose(s) thirty minutes prior to testing. All drugs were dissolved in saline (0.9%; w/v) and delivered intraperitoneally in a volume equal to 1 percent of body weight. Animals failing to show tonic hindlimb extension were scored as protected from MES-induced convulsions.

In summary, it has been discovered that dextromethorphan potentiates the activity of anticonvulsants that do not inhibit or enhance [$^3$H]dextromethorphan binding to the dextromethorphan receptor. Specifically, the examples here demonstrate that dextromethorphan potentiates the anticonvulsant effects of carbamazepine and CPP. The anticonvulsant action of CPP may result from its potent antagonist effects at the N-methyl-D-aspartate subtype of excitatory amino acid receptors. Carbamazepine's mechanism of action is unknown, but may be related to its effects on neutronal ion flux. Dextromethorphan and its metabolites are known to bind at phencyclidine-labeled/N-methyl-D-asparate linked receptors, and is also known to block calcium-induced spasms in smooth muscle. Thus, the action of dextromethorphan or phencyclidine receptors or ion channels may contribute to the dextromethorphan potentiation of carbamazepine and CPP anticonvulsant effects.

Regardless of which mechanism proves correct, the findings described here are novel, and contrary to Tortella and Musacchio's suggestion that the potentiating effects of dextromethorphan, and related compounds, are limited to anticonvulsants that inhibit or enhance [$^3$H]dextromethorphan binding to the [$^3$H]dextromethorphan labeled receptor. Rather, the present discovery indicates that dextromethorphan and other compounds that compete for the dextromethorphan receptor site will potentiate the effects of a range of anticonvulsant compounds, including but not limited to excitatory amino acid antagaonists and carbamazepine, regardless of whether or not the anticonvulsants inhibit or enhance binding at the [$^3$H]dextromethorphan site.

Potentiating agents like dextromethorphan that inhibit or enhance [$^3$H]dextromethorphan binding and that may potentiate the activity of such anticonvulsants include but are not limited to benztropine, chlorpromazine, perphenazine, fluphenazine, cinnarizine, trifluoperazine, prochlorperazine, alpha-flupentixol, trimeprazine, dimethoxanate, opipramol, promethazine, pipazethate, carbetapentane, caramiphen, and noscapine as well as pharmaceutically acceptable derivatives, homologs, isomers, analogs and organic and inorganic salts thereof. The preferred compounds have anticonvulsant acvitity independent of their potentiating action and include perphenazine, fluphanzine, trifluperazine, opipral, carbetapentane and cinnarizine.

The experiments and data as described above demonstrate the ability of dextromethorphan to effectively potentiate anticonvulsant drugs. The potentiating effects of dextromethorphan permit the amount of the anticonvulsant drug necessary to prevent or control convulsions to be reduced. As a result the adverse side effects of the anticonvulsants can be reduced thereby simplifying the treatment procedures and allowing greater versatility of the drugs.

In the preferred form of the invention the potentiating agent and the anticonvulsants are administered to the patient simultaneously and in the same dosage form. Although simultaneous administration is preferred the compounds may be introduced sequentially or in any medically accepted order necessary to achieve the optimal control of seizures. The preferred route of administration is oral but any medically accepted route of administration may be employed.

The anticonvulsant combination according to the present invention can be a liquid oral dose in the form of solutions and suspensions. In making solutions and suspensions the active ingredients are generally dissolved or suspended in distilled water containing a small amount of alcohol to facilitate suspension. Additionally, conventional syrup formulations or any other pharmaceutically acceptable liquid carrier may be employed.

Similarly, for partenteral administration the novel compounds are dissolved in a suitable pharmaceutically acceptable injectable carrier liquid. In the preferred form of the invention the carrier liquid is polyethylene glycol and alcohol.

Alternatively the composition may be introduced as an oral dose in a solid form such as a tablet, pill or capsule. The tablets or capsules may be coated as desired to allow the tablets to be easily swallowed and to provide flavoring. Coatings commonly employed in the pharmaceutical industry may be applied from aqueous suspensions of sugar and insoluble powders such as starch, calcium carbonate, talc or titanium dioxide suspended with a suitable mixing agent such as gelatin. Additional coatings may be applied as desired including water soluble or dispersible material such as hydroxymethylcellulose, cellulose, methylcellulose, carboxymethylcellulose and mixtures of cellulose acetate and polyethylene glycol. In addition, the suitable dosage form may be a capsule formed from commonly employed materials.

In the oral dosage form, the components are generally compounded with inert fillers such as talc, lactose, starch, bentonite, diatomaceous earth, lubricants and food flavorings. The tablets are generally formed by conventional procedures including compressing or molding.

The novel composition according to the present invention is used primarily for the treatment of convulsions and in particular epilepsy. In the preferred form of the invention dextromethorphan or one of its similarly related compounds is combined with an anticonvulsant in a proportion whereby the activity of the anticonvulsant is potentiated which permits a reduction in the amount of the anticonvulsant necessary for effective treatment. By reducing the amount of the anticonvulsant compound necessary for effective treatment the adverse side effects often associated with the known anticonvulsants can be significantly reduced.

The potentiating effect of dextromethorphan and the related compounds varies with the anticonvulsants used. The amount of potentiator compound used should at least be sufficient to potentiate the anticonvulsants and to lower the minimum effective dose of the anticonvulsant.

The type and severity of the convulsions experienced by the patient will also determine the amount of the composition administered. The ratio of the potentiating agent to the anticonvulsant and the effectiveness of the anticonvulsant will determine the amount and form of the composition to be administered to the patient.

The detailed description of the invention is provided primarily for purposes of illustrating the preferred embodiment of the invention. It will be recognized by those skilled in the art that the preferred embodiment is not intended to limit the present invention to the particular compositions and methods of the preferred embodiment as set forth above as they may be readily modified by those skilled in the art. It will further be apparent to those skilled in the art that numerous other modifications not mentioned herein can still be made without departing from the spirit and scope of the invention as described in the following claims.

What is claimed is:

1. A method of treating epilepsy and other convulsions including administering an effective amount of a pharmaceutical composition comprising:
   (a) an effective amount of about 80 mg to 1600 mg per day of an anticonvulsant compound that does not bind to the central nervous system dextromethorphan receptor site; and
   (b) an effective amount of a potentiating agent that binds to the dextromethorphan receptor site selected from the group consisting of dextromethorphan, benztropine, caramiphen, carbetapentane, chlorpromazine, dimethoxanate, flupenthixol, fluphenazine, opipramol, perphenazine, pipazethate, prochlorperazine, promethazine, trifluoperazine, trimeprazine, noscapine, cinnarizine, phenylamine and the pharmaceutically acceptable salts thereof.

2. The method of claim 1 wherein said anticonvulsant compound is carbamazepine.

3. A method of treating convulsions in an animal including administering:
   (a) an anticonvulsant dosage of about 80 mg to 1600 mg per day of carbamazepine; and
   (b) an effective amount of a potentiating agent selected from the group consisting of dextromethorphan, benztropine, caramiphen, carbetapentane, chlorpromazine, dimethoxanate, flupenthixol, fluphenazine, opipramol, perphenazine, pipazethate, prochlorperazine, promethazine, trifluoperazine, trimeprazine, noscapine, cinnarizine, phenylamine and the pharmaceutically acceptable salts thereof.

4. The method of claim 3 wherein said potentiating agent is dextromethorphan.

5. The method of claim 2 wherein said carbamazepine is administered in an amount of about 400 mg to 1600 mg per day.

6. An anticonvulsant pharmaceutical composition comprising:
   (a) an anticonvulsant dosage of about 80 mg to 1600 mg per day carbamazepine; and
   (b) an effective amount of a potentiating agent selected from the group consisting of dextromethorphan, benztropine, caramiphen, carbetapentane, chlorpromazine, dimethoxanate, flupenthixol, fluphenazine, opipramol, perphenazine, pipazethate, prochlorperazine, promethazine, trifluoperazine, trimeprazine, noscapine, cinnariazine, phenylamine and the pharmaceutically acceptable salts thereof.

7. The anticonvulsant pharmaceutical composition of claim 6 wherein said potentiating agent is dextromethorphan.

8. An anticonvulsant composition comprising:
   (a) an effective potentiating amount of dextromethorphan, benztropine, caramiphen, carbetapentane, chlorpromazine, dimethoxanate, flupenthixol, fluphenazine, opipramol, perphenazine, pipazethate, prochlorperazine, promethaine, trifluoperazine, trimeprazine, noscapine, cinnarizine and phenylamine; and
   (b) an anticonvulsant dosage of about 80 mg to 1600 mg per day of carbamazepine, 9. An anticonvulsant pharmaceutical composition comprising:
   (a) an 80 mg to 1600 mg per day dosage of carbamazepine or other anticonvulsant which is capable of binding to the N-methyl-D-aspartate receptor site; and
   (b) a potentiating amount of dextromethorphan, benztropine, caramiphen, carbetapentane, chlorpromazine, dimethoxanate, flupenthixol, fluphenazine, opipramol, perphenazine, pipazethate, prochlorperazine, promethazine, trifluoperazine, trimeprazine, noscapine, cinnarizine, phenylamine and pharmaceutically acceptable salts thereof.

10. The anticonvulsant pharmaceutical composition of claim 6 wherein said anticonvulsant dosage is about 400 mg to 600 mg per day of carbamazepine.

* * * * *